United States Patent [19]

Leeper

[11] 4,435,180
[45] Mar. 6, 1984

[54] ELASTOMERIC ACTIVE AGENT DELIVERY SYSTEM AND METHOD OF USE

[75] Inventor: Harold M. Leeper, Mountain View, Calif.

[73] Assignee: ALZA Corporation, Palo Alto, Calif.

[21] Appl. No.: 381,994

[22] Filed: May 25, 1982

[51] Int. Cl.³ .............................................. A61K 9/00
[52] U.S. Cl. .................................................. 604/896
[58] Field of Search ............... 604/890, 891, 892, 893, 604/897, 896; 424/20–28; 3/1; 168/2; 2/1, DIG. 7

[56] References Cited

U.S. PATENT DOCUMENTS

| | | | |
|---|---|---|---|
| 2,693,438 | 11/1954 | Ward | 167/84 |
| 3,200,037 | 8/1965 | Curtay et al. | 167/62 |
| 3,249,109 | 5/1966 | Maeth et al. | 128/268 |
| 3,279,996 | 10/1966 | Long et al. | 167/82 |
| 3,328,259 | 6/1967 | Anderson | 167/84 |
| 3,339,546 | 9/1967 | Chen | 128/156 |
| 3,598,122 | 8/1971 | Zaffaroni | 424/20 |
| 4,012,497 | 3/1977 | Schopflin | 604/891 |
| 4,289,749 | 9/1981 | Keith et al. | 424/22 |

Primary Examiner—C. Fred Rosenbaum
Assistant Examiner—T. J. Wallen
Attorney, Agent, or Firm—Steven F. Stone; Edward L. Mandell; Paul L. Sabatine

[57] ABSTRACT

A transdermal therapeutic system is formed from a body member surrounding means at least a portion of which is an active agent loaded elastomer which is in a stretched condition during use. The tension created by the stretching of the elastomer is preferably from 20 to 35 psi and maintains the agent transferring contact between the skin and the transdermal therapeutic system. The transdermal therapeutic system may be in the form of a glove, sock, sleeve, cuff or band, for example.

14 Claims, 6 Drawing Figures

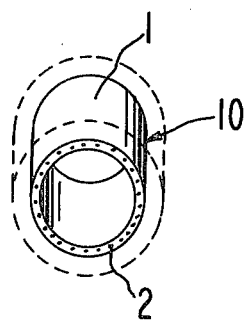
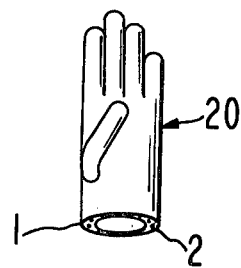
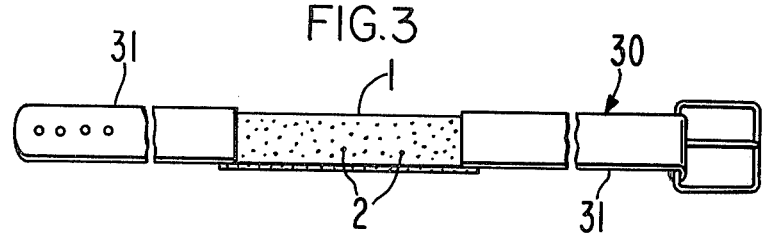
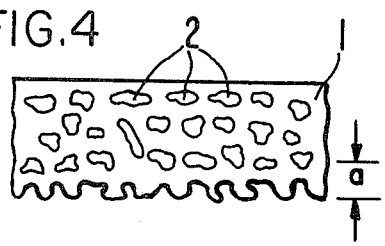
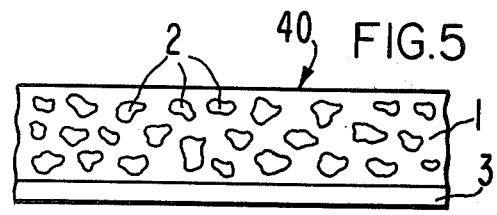
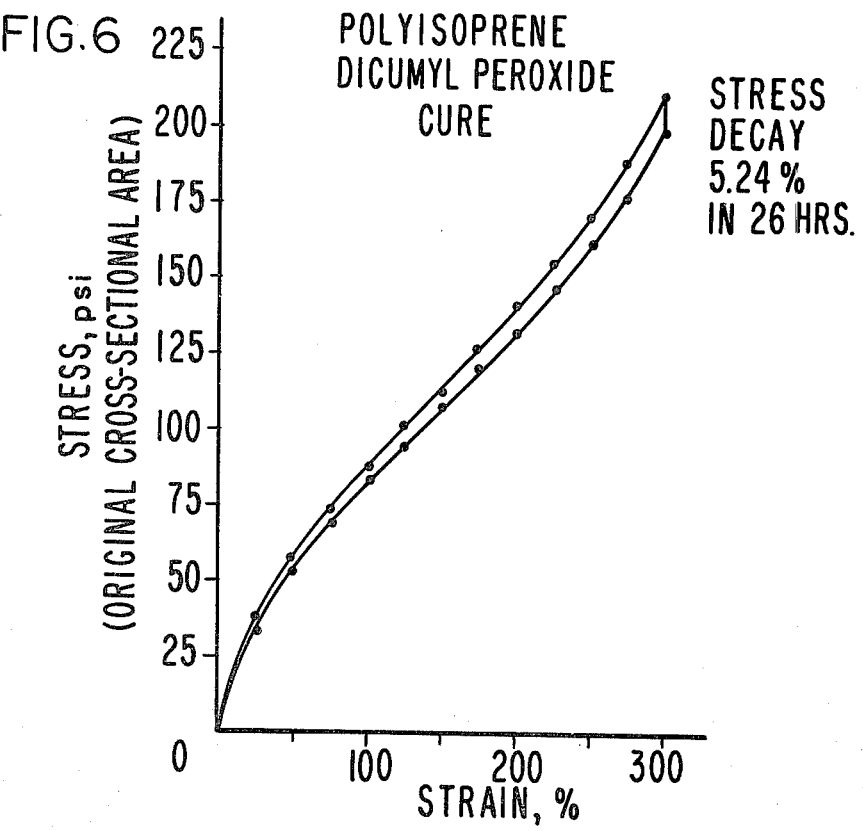

ELASTOMERIC ACTIVE AGENT DELIVERY SYSTEM AND METHOD OF USE

FIELD OF THE INVENTION

This invention relates to devices for delivering an active agent to the skin and more particularly to an elastomeric, monolithic transdermal therapeutic system.

BACKGROUND OF THE INVENTION

This invention relates to an article of manufacture for delivering drug or other active agent to the body through the skin for the production of a beneficial or therapeutic effect. In the past, various devices have been proposed for accomplishing such purposes and these range from adhesive bandages containing topical and systemically acting agents such as are disclosed in U.S. Pat. No. 3,249,109 Maeth, et al., U.S. Pat. No. 3,339,546 Chen or U.S. Pat. No. 3,598,122 Zaffaroni. In lieu of using an adhesive to maintain such a bandage in contact with the skin, it has been suggested that a source of a drug be maintained in contact with the skin by means of a rubber band such as is disclosed in U.S. Pat. No. 4,289,749 Keith, et al. It has also been proposed that a medicament impregnated fabric in the form of a cuff or sock be maintained in contact with the skin by means of resilient rubber threads woven into the fabric such as disclosed in U.S. Pat. No. 3,200,037 Curtay. Other approaches to delivering drugs to the external surface of the body include the concept of forming a glove from a film-like material which contains a medicament such as disclosed in U.S. Pat. No. 2,693,438 Ward and U.S. Pat. No. 3,328,259 Anderson. While all of the above concepts have the capability of delivering the active agent to the skin, problems exist either with respect to cost, complexity or capability of consistent performance. Thus, adhesive bandages require a separate adhesive material interposed between the active agent source and the skin, which adhesive must combine the necessary chemical and physical compatability with the active agent with appropriate adhesive characteristics. Woven fabrics require the formation of a fabric of dissimilar materials and the subsequent impregnation of the fabric with a suitable active agent. The use of a rubber band to hold an active agent reservoir in place requires at least two elements and may be susceptible to separation or displacement of the rubber band from the reservoir. With respect to medicated films in the form of gloves, cuffs or sleeves, they are typically formed in situ or are intended primarily for covering burnt or wounded skin and are dependent upon the adhesive characteristics of the film, their water solubility or the presence of a thermoplastic material softenable at room temperature to maintain the required contact between the glove and the body.

While it is known that rubber matrices having a drug dispersed within or confined inside their structure are useable as implantable drug reservoirs, such as is shown in U.S. Pat. No. 3,279,996 to Long for example, it has not heretofore been proposed or suggested that the elastic properties of elastomeric active agent containing structures be utilized as the means for maintaining the active agent releasing surface of the elastomeric device in close and intimate contact with the skin as a transdermal therapeutic system.

According to this invention, an elastomeric structure adapted to encircle or enclose a body member is provided which elastomeric structure has dispersed therethrough a quantity of active agent adapted to be dispensed to the skin and which elastomeric structure is maintained in contact with the skin primarily as a result of the elastic action of the structure itself. The therapeutic system of this invention is extremely simple to fabricate, can be made in many forms including bands adapted to encircle a body member such as a finger, leg or arm; cuffs adapted to encircle a joint such as an elbow, knee or shoulder; or gloves or socks adapted to completely enclose a hand or a foot, or as an elastic link in a belt, bracelet or band for example. By fabricating the elastomeric structure, such that in its relaxed condition, it is smaller than in its condition of use, the elastic force obviates the need for any adhesive to provide a firm contact between the therapeutic system and the skin thereby substantially simplifying the design and construction of the device as well as its subsequent removal and reuse. Further, by choosing rubbers exhibiting low stress relaxation properties a reusable device can be provided and rubbers exhibiting relatively constant stress-strain characteristics will be usable to produce a device which is adaptable to relatively wide range of body-member sizes without being too loose on small diameters or too tight on larger diameters.

It is accordingly an object of this invention to provide an elastomeric transdermal therapeutic system in which the elastic properties of the device itself provide the means for maintaining the device in contact with the skin.

It is another object of this invention to provide an elastomeric transdermal therapeutic system having a size, in its relaxed condition, which is smaller than its size in its condition of use.

It is another object of this invention to provide a monolithic, elastomeric transdermal therapeutic system.

It is another object of this invention to provide an elastomeric transdermal therapeutic system which may be applied and removed repeatedly.

It is another object of this invention to provide an elastomeric transdermal therapeutic system usable on a range of body member sizes.

These and other object of the invention will be readily apparent from the following description with reference to the accompanying drawings wherein:

FIG. 1 is a perspective view of one embodiment of this invention;

FIG. 2 is a perspective view of another embodiment of this invention;

FIG. 3 is a perspective view of another embodiment of this invention;

FIG. 4 is an enlarged cross-sectional view of another embodiment of this invention;

FIG. 5 is an enlarged cross-sectional view of another embodiment of this invention; and FIG. 6 is a typical stress-strain curve of a polyisoprene elastomer usable in this invention.

Referring now to FIG. 1, the simplest embodiment of this invention is shown. A transdermal therapeutic system (TTS) 10, according to this invention comprises body member surrounding means which in this embodiment is a contiguous elastic band formed from a monolithic elastomeric matrix 1 having an active agent 2 (shown by dots which represent active agent depots in the form of small particles of active agent, liquid droplets of active agent; solid, liquid or gelled active agent containing compositions; or active agent containing microcapsules, for example) dispersed therethrough. As shown in FIG. 1, the device is illustrated in solid lines in its relaxed, stress-free condition and in dotted lines as it would appear in its condition of use when applied around a body member, such as a finger, arm, or leg, for example. The tension generated by stretching the elastic member from its relaxed condition to its condition of use is the means which maintains the internal surface of the TTS in intimate contact with the skin to permit transference of the active agent from the TTS to the body. The tension should be sufficient to maintain intimate contact between the agent releasing surface of the TTS and the skin without being so high as to cause discomfort or to reduce circulation. Generally adequate contact can be obtained when the stress on the elastomer is at least about 10 psi and discomfort is experienced above about 50 psi. Thus preferred range is from about 20 psi to 35 psi. The degree of extension from its relaxed condition to condition of use to achieve the desired stress will vary somewhat depending on the characteristics of the elastomer but generally will be in the range of from about 5-50% and preferably from about 10-20%.

It should be noted at this point that the invention disclosed herein is not dependent on any particular combination of active agent and elastomer, it being understood that any active agent which is capable of being administered to and through the skin can be dispersed within any elastomeric matrix which is chemically compatible therewith and capable of permitting the active agent to pass through the structure by diffusion or otherwise in an amount which, when taken in combination with the effective surface area of the device, is sufficient to produce the desired therapeutic or other beneficial effect. The invention contemplates the use of any elastomeric polymer composition provided that when the elastomeric matrix is combined with the active agent, the resulting product will release the agent at the desired rate for the desired period of time, and provided further that the agent can be incorporated into the elastomeric structure without chemical decomposition, degradation or undesired side reaction. Within the broad scope so defined, it is believed well within the skill of the art to select particular active agent/elastomer combinations from the large number of natural and synthetic rubbers that can produce the desired results according to this invention.

In general, however, the following natural and synthetic elastomeric materials are specifically contemplated for use herein: Polybutadiene rubbers, polyisoprene rubbers, polyisobutylene rubbers, natural rubbers, polyurethane rubbers, silicone rubbers, copolymers of vinyl acetate and alkyl acrylates respectively with ethylenicly unsaturated monomers, butadiene/styrene copolymers, butadiene/acrylonitrile copolymers, polychloroprene rubbers, chlorinated polyethylene rubbers, polyepichlorohydrin rubbers, ethylene/propylene copolymer rubbers, ethylene/propylene/diene monomer rubbers and elastomeric polyesters, for example. In addition, it is contemplated that blends of various elastomers with each other can be used to produce an elastomeric matrix whose overall properties may be more precisely controlled than by the use of only one elastomer.

Various means for incorporating active agent into an elastomeric polymer can be employed as is known to the art. Thus, for example with elastomers such as natural rubber or other rubbers which are fabricated from a gum stock which is subsequently vulcanized, the active agent could be mixed with the gum stock, together with other additives such as plasticizers, softeners, tackifiers, adjuvants and drug release rate modifiers, by conventional roll milling or enclosed intensive mixing followed by the standard vulcanization. If the conditions of milling and vulcanization are such that they could adversely affect a particular active agent such as a nitroglycerine formulation, it is contemplated that the active agent could be admixed with a liquid prepolymer, such as Silastic ®382 for example, and other additives as noted above and subject to a cure or cross linking reaction by the addition of the appropriate curing agent such as stannous octate for the Silastic 382 example. It is also contemplated that the active agent could be mixed with an aqeuous latex mixture and thereafter cast and cured in conventional low temperature manner.

While the above fabrication methods contemplate the inclusion of the active agent within the elastomeric matrix prior to vulcanization or curing, it is also possible to incorporate the agent into the already formed and vulcanized or cured elastomeric structure by imbibition such as is described in the Long patent noted above. Thus, various techniques are known to the art by which an active agent can be incorporated into an elastomeric matrix and it is believed to be within the skill of the art to select the particular fabrication method most suitable for a particular active agent/elastomer system.

In most cases, it is desirable, that the active agent be present in the elastomeric matrix at concentrations higher than the saturation level of the agent in the matrix. The thus formed depots of dispersed active agent act as reservoirs for providing agent to the matrix to replace the agent that diffuses from the monolith to the skin and thence into the circulation. This permits a longer extended lifetime for the device and also, under certain circumstances, as will be more fully described below, permits the attainment of a zero-order release rate.

While, as noted above, various elastomers are contemplated for use with the invention; certain elastomers have desirable characteristics which make their use under certain circumstances preferred. Thus, for example, polybutadienes by virtue of their relatively low glass transition temperatures are generally more permeable to active agents than rubbers such as polyisobutylene and are therefore preferred in high delivery rate systems. Also polybutadienes more readily accept modifiers such as tackifiers, softeners and various adjuvants. On the other hand, certain rubbers such as polyisoprene rubber with a monosulfidic cross-link or a primary valence, carbon-to-carbon crosslink are known to exhibit a relatively low stress decay and a relatively constant stress-strain relationship. FIG. 6 shows the typical stress-strain relationship of such elastomers on the first extension-hold-contraction cycle. In the range between 10%-20% elongation, the stress increases from about 25 psi to about 35 psi. Thus one size device can accommodate a significant variation in body member sizes while providing adequate contact for active agent delivery without producing discomfort or impairment of circulation.

The stress relaxation which occurs on standing in the stressed condition is represented by the distance between the upper and lower portions of the curve. Since this is relatively low there is no significant decrease in the force exerted on the skin during the time the device is worn and it may be removed and reapplied without significant degradation (about 10% or less) of stress.

These characteristics provided an end product with which the pressure exerted on the skin can remain relatively constant over a range of sizes of the body member around which it will be applied and which is also capable of being removed and reused without substantial deterioration of its elastomeric properties.

Certain polyisoprene rubbers and other natural and synthetic rubbers can be subjected to low temperature vulcanization without the side effects resulting from high temperature vulcanization or the shear stress encountered in milling and are therefore also useful for delivering sensitive active agents such as nitroglycerine.

Regardless of the mixing or vulcanization techniques employed, conventional methods exist by which the elastomeric matrix produced can be formed into any desirable configuration. Suitable techniques include molding, casting, extrusion and cutting, for example, to produce elastomeric bands, gloves, socks, sleeves, tubes, and sheets or other elastic articles.

Referring now to FIG. 2, a transdermal therapeutic system 20 according to this invention comprises body member surrounding means consisting of an elastomeric matrix 1 having active agent 2 dispersed therethrough which matrix is formed into the shape of a glove (or a sock for the foot). The glove in its relaxed condition as shown is smaller than the hand to which it is to be applied such that a compressive force will be applied to the fingers and hand to maintain the glove in intimate contact with the skin while it is dispensing its active agent. The use of a glove or a sock is particularly useful for the dispensing of anaesthetic, analgesic, anti-arthritic or anti-inflammatory agents for the treatment of soreness or swelling of the joints of the foot or hand. Such a device is conveniently formed using standard latex technology commonly employed in the formation of surgical gloves with the active agent and other adjuvants or additives added to the latex prior to casting and curing. Alternatively, the glove may be formed in the conventional manner and the active agent thereafter loaded into the elastomer by imbibition from a solution of active agent in a solvent which has a swelling action on the elastomer and which may later be removed by evaporation.

In certain situations, such as where the skin contacting surface area of a tubular TTS may be so high as to deliver too much active agent for example; the drug loaded elastomer may be a link or a portion of the body member surrounding means. Thus as shown in FIG. 3 a TTS 30 comprises monolithic elastomeric matrix 1 having dispersed active agent depots 2 which is bonded, glued, stitched or otherwise firmly attached to one or more body encircling elements 31 here shown as a belt and buckle. In use the TTS 30 could be appended around a body member such as a wrist and tightened to stretch matrix 1 to produce the desired skin contacting force.

Referring now to FIG. 4, a cross-sectional view of the wall structure of a tubular monolithic TTS according to this invention is shown in which the surface of the TTS which is intended to contact the skin has been treated according to the teachings of U.S. Pat. No. 3,923,939, Baker, et al., for the purpose of improving the release kinetics by the in situ formation of an agent-depleted barrier at the skin proximal surface of the device. Thus as shown in FIG. 3, elastomeric matrix 1 has dispersed therethrough active agent depots 2, but the inner skin contacting surface has been treated to remove the active agent from a portion thereof of thickness "a" which may be up to approximately 5% of the total thickness of the device.

While it is one of the objects of this invention to provide for the fabrication of a simple monolithic TTS, it is also possible to obtain many of the advantages of the invention by utilizing a laminate structure in which the skin contacting, non-skin contacting or bothsurfaces of the TTS are formed from a material having characteristics different from that of the body of the elastomeric TTS. As shown in FIG. 5, a tubular TTS 40 of this invention comprises an elastomeric matrix 1 having active agent depots 2 dispersed therethrough as above described, with one surface of the TTS being a layer 3 bonded or otherwise adheringly or firmly attached to matrix 1 which layer 3 can have any of several functions. In one embodiment of the invention, layer 3 can be a release rate controlling membrane which limits the rate at which drug diffuses from the TTS to the skin such as is disclosed in U.S. Pat. No. 3,996,934 to Zaffaroni. Alternatively, layer 3 could be in the form of a foam or other material which could improve the tactile characteristics of the TTS when placed in contact with the skin or permit greater skin breathing for a TTS which is intended to be maintained on the skin for long periods of time such as several days or longer. In these embodiments layer 3 would be on the skin contacting surface of the elastomeric matrix or such layers could be applied to both sides if desired to prevent the device from being applied backwards. Alternatively layer 3 on the non-skin contacting surface could be an active agent impermeable barrier to prevent release or escape of the agent from the elastomeric matrix other than through the skin contacting surface. In these embodiments the material used for layer 3 should be capable of extending from the relaxed condition in which the device is fabricated and stored to the expanded condition, in which it is adapted to be used, without breaking, tearing, or otherwise deteriorating. The material 3 may be, but need not be, elastomeric since the matrix 1 has the elastic characteristics necessary to maintain the skin contacting pressure on the body surface to which the TTS applied.

Having thus generally described the invention, the following specific examples of various embodiments are provided.

EXAMPLE I

The following composition is prepared by conventional rubber compounding practice on a 2-roll rubber mill.

|  | Parts by Weight |
|---|---|
| Natural rubber, pale crepe | 100 |
| Calcium stearate (processing aid) | 2 |
| Stearic acid (activator of cure) | 2 |
| Zinc oxide (activator of cure) | 5 |
| Alkylated diphenyl amine (antioxidant) | 1 |
| Sulfur (crosslinking agent) | 2.75 |
| Benzothiazyl disulfide (accelerator) | 1 |
| Tetramethyl thiuram disulfide (secondary accelerator) | 0.1 |
| Hydrocortisone alcohol (active agent) | 12.6 |

The blended mix is then extruded into the shape of a round tube of diameter 1.8 inch and thickness 0.06 inch. Appropriate lengths of this tubing are then vulcanized in a steam autoclave at 60 psi (307° F.) for 5 minutes. Following vulcanization the tubing is sliced into bands 0.5 inch in width. These bands then contain 10% drug by weight and are adapted to be applied around an adult ankle to dispense the active agent to systemic circulation for the treatment of inflammatory conditions.

EXAMPLE II

Following vulcanization the tube produced according to Example I is subjected to a slow flow of water to leach active agent from the internal surface to a depth of approximate 3 mils. The effect of the leaching is to improve the active agent release kinetics from a function of $t^{-\frac{1}{2}}$ to a profile more closely approximating $t^0$.

EXAMPLE III

The following composition is prepared by conventional rubber compounding methodology on a 2-roll rubber mill.

|  | Parts by Weight |
|---|---|
| Synthetic cis-polyisoprene | 100 |
| Zinc oxide | 4 |
| Stearic acid | 1 |
| Tetramethyl thiuram disulfide | 4 |
| Ephedrine | 9.5 |

The mixed compound may then be extruded as in Example I or calendered on a 4-roll rubber calendar into a continuous sheet 12 inches in width and 0.02 inch in thickness. It is taken up, with a suitable release liner into roll form, and the roll is vulcanized in a steam autoclave at 38 psi (284° F.) for 3 hours. The resulting extruded tubes may be slit as in Example I or the cured sheet may be slit into strips of desired width and length or any other suitable shape and used to form a TTS as in FIG. 3. The elastomer produced herein has predominantly monosulfidic crosslinks, possesses a relatively low increase of stress with strain and a low stress decay. TTS's produced from this material are suitable for removal and reuse and for application around body members of disparate sizes producing from 5–50% elongation and preferably from 10–20%. The average release rate of ephedrine into water is approximately 2.5 $\mu g/cm^2/hr$.

EXAMPLE IV

Prepare the following composition beginning with natural rubber latex.

|  | Parts by Weight |
|---|---|
| Natural rubber latex, concentrated (68% solids) | 147 |
| Zinc carbonate (50% dispersion in water) | 30 |
| Sulfur (50% dispersion in water) | 6 |
| Zinc dibutyl dithiocarbamate (50% dispersion in water) | 4 |
| Ammonium nitrate (30% in 5% ammonium hydroxide) | 23 |
| Progesterone | 6.7 |

Suitable forms are dipped into this latex compound (such as a form in the shape of a hand) to produce a 15 mil layer, withdrawn, and the deposited film allowed to dry free of water by gentle warming. The dry rubber, while still on the form is then heated in air to 70°–85° C. and allowed to vulcanize for 1–2 hours. The rubber article may then be removed by stretching, from the form. The size of the form is selected to produce an article requiring from 10–20% elongation when applied to the hand. The glove contains 5% progesterone and releases, at equilibrium, approximately 0.1 $\mu g/cm^2/hr$.

EXAMPLE V

A commercial natural rubber band, 1¾ inch lay flat, ⅜" wide was extracted in boiling acetone for 8 hours to remove low molecular weight and acetone soluble impurities. The band was then soaked in acetone containing an excess of estradiol at 45 C. for 72 hours and dried in air at 45 C. for 1.5 hours. The band then contained 1.69% estradiol. The estradiol loaded band was immersed in polyethylene glycol monolaurate (PEGML) saturated with estradiol to load the PEG ML permeation enhancer into the band without extraction of estradiol. The final composition contained 74.6% elastomer matrix, 24.2% PEGML and 1.14% estradiol. The resulting skin controlled TTS provided approximately 0.1 $\mu g/cm^2/hr$ of estradiol. When applied around the average adult female wrist approximately 15% extension should be obtained.

EXAMPLE VI

The following composition is prepared by conventional 2-roll rubber mixing.

|  |  |
|---|---|
| Ethylene/vinyl acetate (EVA) copolymer (40% vinyl acetate) | 100 |
| Aspirin (pure) | 43 |

The above compound mix is coextruded as a tube 0.020 inch thick around a 2 mil thick tube of natural rubber. The thin component of the coextruded laminate is now the rate controlling membrane for release of the asprin from the elastomeric EVA matrix into an infinite sink at a zero order rate of approximately 80 $\mu g/cm^2/hr$.

EXAMPLE VII

The following compound is mixed on a conventional 2-roll rubber mill:

|  | Parts by Weight |
|---|---|
| Synthetic isoprene rubber | 50.00 |
| Butadiene rubber | 50.00 |
| Zinc oxide | 5.00 |
| Stearic acid | 3.00 |
| N—tert-butyl-2-benzothiazole sulfenamide | 0.65 |
| 4,4¹-dithiomorpholine | 0.55 |
| Sulfur | 1.65 |
| Propranolol base | 5.83 |

The compound is fed, in strip form from the rubber mill, into a rubber tubing extruder, and tubing is extruded with a diameter of 2.25 inches and wall thickness 0.020 inch. The uncured tubing is cut into lengths of 48 inches and cured in a steam autoclave for 30 minutes at 287° F. After curing, the tubing is sliced into bands ½ inch in width. The bands may be applied around the forearm to deliver propanolol to the skin at a rate which is a function of $t^{-\frac{1}{2}}$.

EXAMPLE VIII

The following two rubber compositions are mixed on a conventional 2-roll rubber mill:

|  | A | B |
|---|---|---|
| Synthetic isoprene rubber | 100 | 100 |

| | A | B |
|---|---|---|
| Zinc oxide | 3 | 5 |
| Stearic acid | 2 | 3 |
| Tetramethyl thiuram disulfide | 3 | 6 |
| Propranolol | 5.83 | |

The mixed compounds are individually fed, in strip form, to a rubber tubing extruder designed to coextrude two separate compounds simultaneously and continuously into the shape of a dual wall tube 2.25 inches in diameter, compound A being the outerlayer, 20 mils (0.020 inch) thick and compound B being the inner layer, 4 mils thick (0.004 inch). The extruded, uncured tubing is cut into 48 inch lengths, embedded in a talc bath in shallow pans and cured in a steam autoclave for 2 hours at 284° F. The cured tubing is then sliced into bands 0.5 inch in width, and the bands are washed free of surface talc in water. The inner layer will be more highly crosslinked because of the higher level of curative that it contains. It will be the surface proximal to the skin in actual use and will have a lower flux for the drug than the outer, less crosslinked layer which serves as the reservoir for the drug. The inner surface therefore functions as a rate controlling element to permit propranolol release to the skin at a rate which is substantially constant for a significant portion of the useful life of the TTS when applied to the forearm or ankle for example.

Having thus generally and specifically defined my invention, it will be obvious that various modifications to the invention disclosed herein can be made without departing from the scope of this invention, which is limited only by the following claims wherein I claim:

1. A transdermal therapeutic system for delivering active agent to the skin comprising body member surrounding means, at least a portion of said means being formed from an elastomeric matrix having active agent dispersed therethrough at a concentration greater than the saturation concentration of said agent in said elastomer, the skin proximal surface area of said matrix being smaller in its relaxed condition than in its condition of use when applied around a body member whereby the elastomeric matrix creates a compressive force on said body member sufficient to establish and maintain active agent transferring contact between said transdermal therapeutic system and the skin of said body member.

2. The transdermal therapeutic system of claim 1 wherein said elastomer matrix surrounds said body member.

3. The transdermal therapeutic system of claim 1 wherein said elastomer matrix comprises material selected from the group consisting of natural rubbers, synthetic elastomers and mixtures thereof.

4. The transdermal therapeutic system of claim 3 wherein said synthetic elastomers are selected from the group consisting of polybutadiene, polyisoprene, polyisobutylene, polyurethane, ethylene/propylene, ethylene/propylene/diene, polyester, polychloroprene, chlorinated polyethylene, polyepichlorohydrin, and silicone rubbers; copolymers of vinyl acetate and ethylene, alkyl acrylates and ethylene, butadiene and styrene, butadiene and acrylonitrile and mixtures thereof.

5. The transdermal therapeutic system of claim 2 wherein the elongation of said matrix from its relaxed condition to its condition of use produces a stress of from about 10 to 50 psi.

6. The transdermal therapeutic system of claim 5 wherein said stress is from 20 to 35 psi.

7. The transdermal therapeutic system of claim 5 or 6 wherein said elastomeric exhibits a relatively low stress decay within the range of elongation.

8. The transdermal therapeutic system of claim 1 wherein the skin proximal surface of said elastomer matrix is provided with means for controlling rate of release of said agent.

9. The therapeutic system of claim 1 wherein said structure is in the form of a sock.

10. The elastomeric member of claim 1 wherein the elastomer is in the form of a tubular sheath.

11. The elastomeric member of claim 1 wherein the member is in the form of a glove.

12. A method for delivering active agent to the skin which comprises applying around a body member an active agent delivery device, at least a portion of which is an elastomeric element, loaded with an active agent at a concentration above the saturation concentration of said agent in said elastomeric element and maintaining said elastomeric element in contact with the skin and in tension during the period of active agent delivery whereby the stress produced by said elastomeric element provides active agent transferring contact between the skin and the elastomeric element.

13. The method of claim 12 wherein the stress in the elastomer is in the range of from 10 to 50 psi.

14. The method of claim 13 wherein the stress is in the range of from 20–35 psi.

* * * * *